US012797448B2

(12) United States Patent
Kaviraj et al.

(10) Patent No.: US 12,797,448 B2
(45) Date of Patent: Nov. 17, 2026

(54) LYOPHILISED FORMULATIONS OF MRNA ADSORBED ONTO LIPID NANO-EMULSION PARTICLES

(71) Applicant: GENNOVA BIOPHARMACEUTICALS LTD., Pune (IN)

(72) Inventors: Swarnendu Kaviraj, Pune (IN); Sanjay Singh, Pune (IN); Sunil Raut, Pune (IN); Pavan Kardile, Pune (IN); Ajay Singh, Pune (IN)

(73) Assignee: GENNOVA BIOPHARMACEUTICALS LTD, Pune (IN)

( * ) Notice: Subject to any disclaimer, the term of this patent is extended or adjusted under 35 U.S.C. 154(b) by 178 days.

(21) Appl. No.: 18/686,065

(22) PCT Filed: Aug. 24, 2022

(86) PCT No.: PCT/IN2022/050753
§ 371 (c)(1),
(2) Date: Feb. 23, 2024

(87) PCT Pub. No.: WO2023/026301
PCT Pub. Date: Mar. 2, 2023

(65) Prior Publication Data

US 2024/0350413 A1 Oct. 24, 2024

(30) Foreign Application Priority Data

Aug. 25, 2021 (IN) ............................ 202121038492

(51) Int. Cl.

| | |
|---|---|
| ***A61K 39/00*** | (2006.01) |
| ***A61K 9/107*** | (2006.01) |
| ***A61K 9/14*** | (2006.01) |
| ***A61K 9/19*** | (2006.01) |
| ***A61K 39/215*** | (2006.01) |
| ***A61P 31/14*** | (2006.01) |

(52) U.S. Cl.
CPC ............ *A61K 39/00* (2013.01); *A61K 9/1075* (2013.01); *A61K 9/145* (2013.01); *A61K 9/19* (2013.01); *A61K 39/215* (2013.01); *A61P 31/14* (2018.01); *A61K 2039/51* (2013.01); *A61K 2039/552* (2013.01); *A61K 2039/55555* (2013.01); *C12N 2770/20034* (2013.01)

(58) Field of Classification Search
None
See application file for complete search history.

(56) References Cited

U.S. PATENT DOCUMENTS

2020/0383922 A1* 12/2020 Ketterer .................. A61P 27/02

OTHER PUBLICATIONS

Is mRNA-1273 a non-replicating replicon mRNA transcript—Google Search (Year: 2026).*
Xiaojie et al.; Neutralizing antibodies targeting SARS-CoV-2 spike protein; Elsevier; Stem Cell Research 50 (2021) 102125 (Year: 2021).*
Gerhardt et al.; A Thermostable, Flexible RNA Vaccine Delivery Platform for Pandemic Response; 2021; bioRxiv (preprint) (Year: 2021).*
Anderson et al.; Safety and Immunogenicity of SARS-CoV-2 mRNA-1273 Vaccine in Older Adults; Massachusetts Medical Society; n engl j med 383;25 nejm.org Dec. 17, 2020 2427-2438 (Year: 2020).*
What is room temperature in Germany—Google Search (Year: 2026).*
Is mRNA-1273 capable of expression spike protein—Google Search (Year: 2026).*
Search Report and Written Opinion for PCT Application No. PCT/IN2022/050753, mailed on Nov. 29, 2022, 8 pages.
Anderson , et al., Safety and immunogenicity 2 4, 27, 28 of SARS-CoV-2 mRNA-1273 vaccine in older adults. N. Engl. J. Med. , 383, 2427-2438 (2020).
Gerhardt , et al., A Thermostable, Flexible RNA 1-23, 25, 26 Vaccine Delivery Platform for Pandemic Response, Feb. 2, 2021, bioRxiv 2021.02.01.429283; doi: https://doi.org/10.1101/2021.02.01.429283.
Polack , et al., Safety and efficacy of the 2 4, 27, 28 BNT162b2 mRNA Covid-19 vaccine. N. Engl. J. Med., 383, 2603-2615 (2020).

* cited by examiner

*Primary Examiner* — Robert A Wax
*Assistant Examiner* — John W Lippert, III
(74) *Attorney, Agent, or Firm* — Merchant & Gould P.C.

(57) ABSTRACT

Lyophilised formulations of mRNA adsorbed onto lipid nano-emulsion particles. The present invention relates to lyophilised formulations of mRNA adsorbed onto lipid nano-emulsion particles. It particularly provides a method for lyophilisation of liquid 5 formulations of mRNA adsorbed onto lipid nano-emulsion particles under the conditions that maintain the integrity and pharmaceutical properties of resultant lyophilised formulations for the extended periods at storage temperature of about 5 °C.

16 Claims, 5 Drawing Sheets

LYOPHILISED FORMULATIONS OF MRNA ADSORBED ONTO LIPID NANO-EMULSION PARTICLES

CROSS-REFERENCE TO RELATED APPLICATIONS

Figure 1:
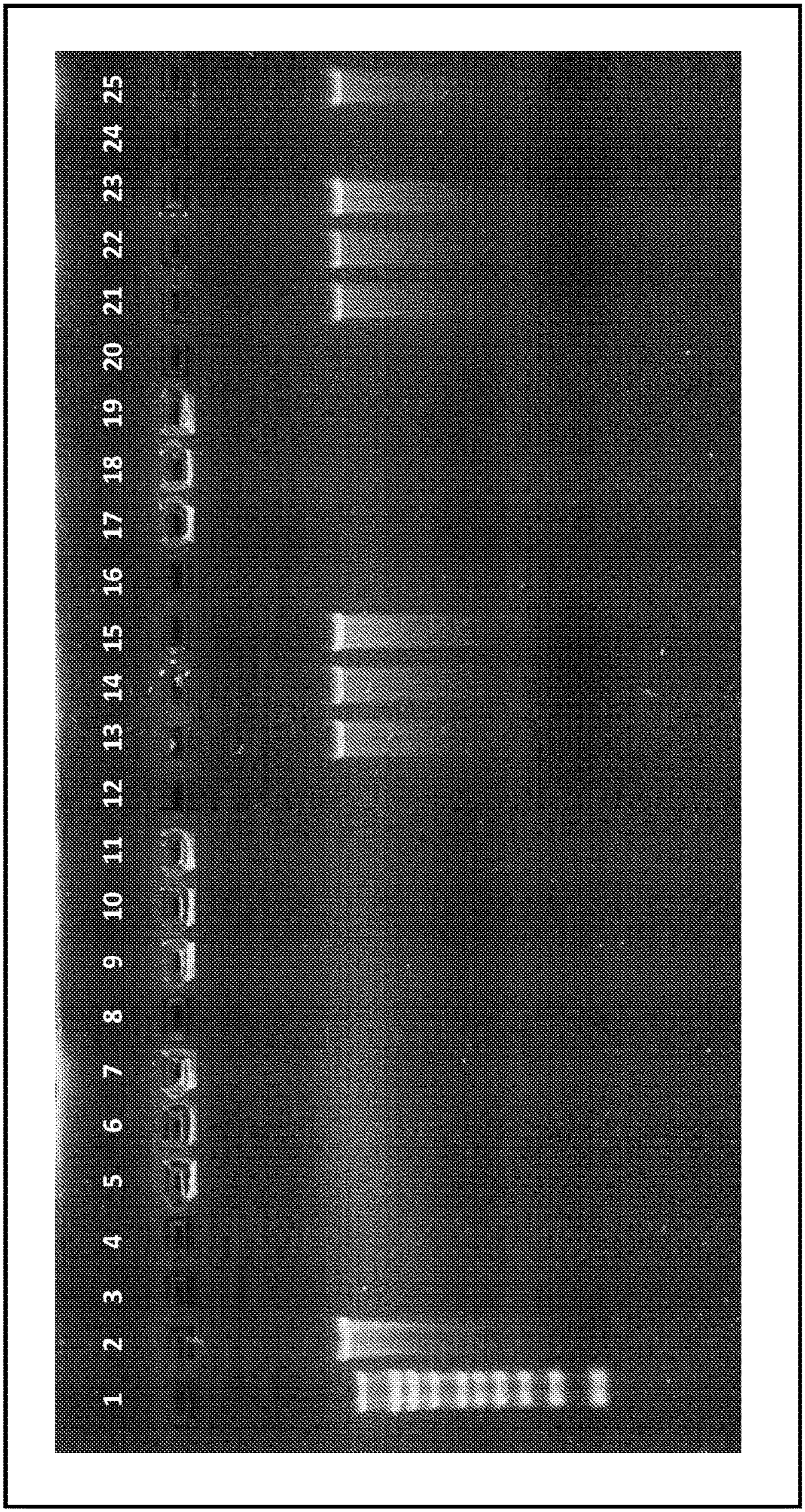

This application is a U.S. National Stage Application under 35 U.S.C. § 371 of International Application No. PCT/IN2022/050753, filed Aug. 24, 2022, which claims priority to an Indian patent application Ser. No. 202121038492, filed Aug. 25, 2021, the disclosure of which is incorporated herein by reference in its entirety.

THE FIELD OF INVENTION

The present invention relates to lyophilised formulations of mRNA adsorbed onto lipid nano-emulsion particles. It particularly provides a method for lyophilisation of liquid formulations of mRNA adsorbed onto lipid nano-emulsion particles under the conditions that maintain the integrity and pharmaceutical properties of resultant lyophilised formulations for the extended periods at storage temperature of about 5 °C.

BACKGROUND

Recently, in many therapeutically relevant pharmaceutical applications, nucleic acids as such are used for therapeutic purposes. As an example, the field of mRNA-based therapy has shown the promising results. Herein various types of mRNA molecules are regarded as important tools for gene therapy as well as prophylactic and therapeutic vaccination against many infectious and malignant diseases.

Nucleic acids, both DNA and mRNA molecules, have been used widely in gene therapy, either in naked or in complexed forms. The use of mRNA is advantageous in modern molecular medicine, which has some superior properties over the use of DNA. As is known, transfection of DNA molecules may lead to serious complications, however, these risks do not occur particularly with mRNA molecules. An advantage of using mRNA rather than DNA is that no virus-derived promoter element has to be administered in vivo and no integration into the genome may occur and further the mRNA does not need to travel to the nucleus for the expression.

Conversely, a main disadvantage of mRNA is its instability and rapid degradation during the production and formulation stages and before delivery to the cytoplasm of the cells. The physico-chemical stability of mRNA molecules in solution is extremely low compared to DNA. The mRNA is susceptible to hydrolysis by ribonucleases or by divalent cations and is typically rapidly degraded within a few hours in solution at room temperature. To avoid such rapid degradation of mRNA it is typically stored between −80 and −20 °C. However, such storage conditions are expensive, especially for shipping and storage of a large amounts of mRNA-based therapeutic or vaccine products.

However, in the art for sensitive biomolecules like mRNA, lyophilisation or freeze-drying is the method of choice. Lyophilisation typically removes water from a frozen sample via sublimation. During lyophilisation, the sample is cooled below the freezing point of water, which then freezes in freezing cycle. This is followed by removal of water by sublimation during drying cycle. However, this freezing/drying of water may lead to crystal formation/loss of hydration around biomolecules, which further damages the biomolecules by a variety of physico-chemical means. Hence, a number of lyoprotectants [a k a cryoprotectants] have been used for the lyophilisation purposes to prevent these damages.

The formulations with mRNA as the API are inherently unstable in aqueous solutions. The shelf life of such formulations is only a few days at room temperature. Lyophilisation or freeze drying is used to such formulations. However, overcome this limitation in lyophilisation process is unpredictable and conditions need to be determined empirically for each formulation, if a large-scale production for said formulations need to be implemented. Even though, freeze drying of mRNA formulations under laboratory conditions have been described, there is still a need for improved methods in this art. In particular, a method is needed that allows industrial application of lyophilisation to complexes like the mRNA molecules adsorbed onto lipid nano-emulsion particles or nano-carriers in liquid.

Thus, an object of the present invention is to provide a method for lyophilisation of mRNA-based complex formulations, which is scalable and reproducible, which is time- and cost-efficient. It is a further object of the invention to provide a freeze-dried formulation comprising mRNA molecules, which is suitable for storage at ambient temperature and over extended periods, and preferably having increased storage stability as compared to prior art formulations, wherein the mRNA molecules having the pharmaceutical value.

DESCRIPTION

The present invention provides a method for lyophilising a liquid formulation of mRNA molecules adsorbed onto lipid nano-emulsion particles or nano-carriers for pharmaceutical applications like vaccines and therapeutics. In particular, the invention relates to a method for lyophilising mRNA adsorbed onto lipid nano-emulsion particles or nano-carriers, wherein said method comprises the stages of:

1) providing a liquid mixture comprising at least one mRNA adsorbed onto lipid nano-emulsion particles and at least one lyoprotectant in a glass vial, loading said glass vial in a freeze dryer chamber and pre-cooling it for a desired temperature and time;
2) cooling said mixture to a freezing temperature in said freeze dryer chamber under a desired cooling rate and holding it for a desired time and then freezing said mixture at said freezing temperature forming a frozen mixture;
3) reducing the pressure in said freeze drying chamber to a pressure below atmospheric pressure in desired two pressure reducing steps and desired three heating steps, and primary drying said frozen mixture;
4) further treating said frozen mixture in said freeze drying chamber to a pressure below atmospheric pressure in a desired pressure reducing step and a desired heating step, and secondary drying said frozen mixture forming a lyophilised formulation comprising the at least one mRNA adsorbed onto lipid nano-emulsion particles and at least one lyoprotectant in said glass vial; and
5) stoppering said glass vial and then equilibrating said freeze drying chamber to atmospheric pressure and temperature under nitrogen gas and removing said glass vial containing said lyophilised formulation for sealing.

In a preferred embodiment, the said lyophilised formulation being stable at temperature of about 5 °C and is capable of generating functional immune response when injected in a subject. Herein, the phrase "at temperature of about 5 °C" means any temperature between 2 and 8 °C, wherever it is being used. Further herein "liquid mixture" means a liquid formulation of the vaccine before its lyophilisation or freeze drying.

In a preferred embodiment, inventive stages 1 to 5 as above are performed sequentially. Moreover, said stages comprise one or more steps and may be performed concomitantly or may overlap.

The invention herein discloses a method of lyophilisation of a formulation of mRNA adsorbed onto lipid nano-emulsion particles in liquid in the presence of a lyoprotectant, preferably a carbohydrate lyoprotectant, preferably selected from the group of carbohydrates consisting of mannitol, sucrose, glucose, mannose or trehalose, and under desired freezing and drying conditions, resulting in a stable formulation, having an outstanding integrity of the mRNA after completion of the lyophilisation process and having increased storage reliability, in particular with respect to storage for extended periods and under non-cooling conditions. Further, said invention is suitable for use at an industrial scale.

In the context of the present invention, previously it was difficult and unreliable to lyophilise mRNA adsorbed onto lipid nano-emulsion particles in liquid in the presence of a lyoprotectant, however, a method disclosed herein leads to such exceptional properties of the formulations according to the invention. Further it is reproducible and cost-effective at an industrial scale. Further, there was no suggestion in the prior art concerning a method for lyophilising adsorbed mRNA complexes or molecules under the freezing and drying conditions as disclosed herein.

In the context of the present invention, the liquid mixture provided in stage 1) comprises a formulation of at least one mRNA adsorbed onto the surfaces of lipid nano-emulsion particles or nano-carriers in liquid along with a lyoprotectant sugar. Such mRNA complexes are produced by a method disclosed herein and include the nano-emulsion particles comprising cationic lipids in water prepared under the controlled condition. The surfaces of the such particles are suitable for adsorption of single-stranded mRNA molecules being negatively charged and said particles are also called nano-carriers.

In a preferred embodiment, the liquid mixture comprises nano-carriers, wherein the particles comprise or consist of at least one cationic lipid compound, wherein the complex is preferably present as a nanoparticle as defined herein. The said nano-carriers further comprise other components like squalene and one or more surfactants like polysorbate −80 or sorbitan monostearate in a buffered stabilized solution along with, optionally, one or more TLR4 agonist adjuvants.

In a preferred embodiment, the liquid mixture provided in stage 1) comprises at least one mRNA adsorbed onto lipid nano-emulsion particles, wherein the size, preferably the average size, of the nanoparticle is in a range from 50 to 500 nm, more preferably from 50 to 300 nm. In a particularly preferred embodiment, the size of the nanoparticle is from 50 to 150 nm.

In a preferred embodiment, the liquid mixture provided in stage 1) of the inventive method comprises water as the solvent, which allows dissolution of further components, such as a lyoprotectant or buffering agents and desired excipients. Herein water is preferably pyrogen-free water or water for injection (WFI).

The liquid provided in stage 1) of the inventive method may comprise a buffer, e.g. a buffer containing citric acid or like buffer. However, any other suitable buffer system can be used for similar effects.

In a preferred embodiment, the liquid mixture provided in stage 1) comprises at least one lyoprotectant, wherein the lyoprotectant is selected from the group of carbohydrates. Such carbohydrates are suitable for the preparation of a pharmaceutical formulation, without being limited thereto, comprise disaccharides, such as sucrose, trehalose, etc. In addition, the sugar preferably has a low tendency to crystallize, such as trehalose. A lyoprotectant in the liquid mixture provided in stage 1) of the inventive method is preferably selected from the group consisting of mannitol, sucrose, glucose, mannose or trehalose.

The weight ratio of the particles in the liquid mixture provided in stage 1) to the lyoprotectant, preferably a carbohydrate, more preferably a sugar, even more preferably sucrose, in said liquid is preferably in a range from 10 to 40 percent and more preferably from 10 to 20 percent.

In one embodiment, the liquid mixture provided in stage 1) of the inventive method comprises at least one mRNA at a concentration of at least 300 μg/mL, and preferably at least 10 μg/mL.

The liquid mixture provided in stage 1) of the inventive method is preferably a liquid or semi-liquid formulation, which comprises at least one mRNA as defined herein and at least one lyoprotectant as defined herein. The at least one mRNA and the at least one lyoprotectant are preferably dissolved in the liquid mixture provided in stage 1), which has 1A) as the step. In a preferred embodiment, the liquid mixture is an aqueous solution of the at least one mRNA and the at least one lyoprotectant, preferably comprising a solvent as defined herein. The liquid mixture, as used herein, may also be a viscous solution, an emulsion, a dispersion, a suspension, or the like. In said step 1A) a vial containing a desired amount of the liquid mixture is subjected to loading in the freeze drying chamber of a lyophiliser. Then said vial is subjected to a pre-cooling preferably from about 25 °C to about 5 °C.

According to the inventive method, the liquid mixture provided in stage 1) is introduced into a freeze drying chamber of a freeze dryer or lyophiliser. Herein, the term 'freeze dryer' refers to an instrument, which allows the lyophilisation of liquid or semi-liquid formulations. Preferably, the freeze dryer as used herein can be controlled with respect to parameters characterizing the lyophilisation process, such as temperature and pressure in a freeze drying chamber, which contains the liquid to be lyophilised. This regulation is preferably performed in a semi-automatic or automatic manner, e.g. by programming the instrument before the beginning of the lyophilisation process so that the instrument performs a desired lyophilisation process, for example by applying certain predetermined steps (e.g. freezing, drying), and preferably the transition from one such step to another, under predetermined temperatures and pressures. It is further, preferred that the freeze dryer comprises a freeze drying chamber, wherein the atmosphere can preferably be controlled, i.e. by flooding the chamber with nitrogen.

According to a preferred embodiment, the liquid mixture after stage 1) is subjected to stage 2) of the method in the freeze drying chamber, wherein step 2A) comprises freezing of the liquid mixture to a sub-zero temperature from about 5 °C, preferably at a temperature in a range from −40 to −60 °C, most preferably at a temperature in a range from −50 to −60 °C with a cooling rate of between about 0.8 and 1.0

°C/min. Next, said liquid mixture is subject to holding at a temperature in a range from −50 to −60 °C for about 500 minutes and more preferably about 300 minutes. Further, in steps 2A) and 2B) comprise the introduction of the liquid mixture into the freeze drying chamber, wherein the pressure in the freeze drying chamber is approximately equal to the pressure according to the standard atmosphere (about 760 mTorr).

The inventive method further comprises a stage 2) of cooling the liquid mixture to a freezing temperature, wherein the cooling is performed at a defined cooling rate [step 2A)] and a step of freezing [step 2B)] the liquid mixture at the freezing temperature in order to obtain a frozen mixture.

In a preferred embodiment, the freezing temperature is a predetermined temperature. With respect to the quality of the lyophilised product, it is important that an appropriate freezing temperature is chosen. In particular, the frozen mixture temperature comprising one mRNA and a lyoprotectant must remain below the collapse temperature of the liquid mixture. According to a preferred embodiment, the freezing temperature in the inventive method is below the collapse temperature of the liquid mixture provided in stage 1) or the frozen mixture obtained in stage 2), respectively.

In a further preferred embodiment, the freezing temperature is equal to or lower than the glass transition temperature of the liquid mixture provided in stage 1) or the frozen mixture obtained in stage 2), respectively.

The temperatures defined herein with respect to the inventive method typically refer to the respective temperatures in the freeze drying chamber. The temperature in the freeze drying chamber is preferably determined by determining the shelf temperature, the temperature of the liquid mixture provided in stage 1) or the frozen mixture obtained in stage 2), respectively, or the temperature of a portion thereof. As used herein, the term 'shelf temperature' typically relates to the temperature as measured via at least one probe, which is preferably positioned on the surface of the shelf. The temperatures of the liquid mixture provided in stage 1) and the frozen mixture obtained in stage 2), or the temperatures of a portion thereof, preferably correspond to the respective shelf temperatures.

In a preferred embodiment, the lyophilisation is controlled by using the shelf temperature as a parameter. For example, a lyophilisation process is typically programmed by using the temperatures as defined herein as shelf temperatures and as illustrated in the TABLES under section EXAMPLES. Optionally, the actual temperature of the liquid mixture provided in stage 1) and/or the frozen mixture obtained in stage 2), or a portion thereof, may be measured directly, e.g. during the establishment of a production process, in addition to the shelf temperature.

According to a preferred embodiment, stage 2) of the inventive method comprises cooling the liquid mixture provided in stage 1) to a freezing temperature, wherein the cooling rate is defined rate. Preferably, the cooling rate in stage 2) is less than 1.5 °C/min. Alternatively, the cooling rate in stage 2) may be in a range from 0.05 to 1.0 °C/min.

In a specific embodiment of the inventive method, the freezing temperature is maintained for at least 200 minutes, more preferably for at least 300 minutes and most preferably for at least 500 minutes.

The method of the invention further comprises stage 3) of primary drying, which comprises reducing the pressure in the freeze drying chamber to a pressure below atmospheric pressure [step 3A)] about 100 mTorr and holding it [step 3B)] at the pressure for a desired time and then in next step [step 3C)] increasing the temperature from about −60 to about −40 °C at a rate between 0.05 and 0.09 °C/min and holding as that temperature for a desired time [step 3D)]. In further next step [step 3E)] the pressure is reduced to about 75 mTorr and the temperature is increased to about −20 °C at a rate between 0.05 and 0.09 °C/min (e.g. 0.07 °C/min), and this position is held for a desired time [step 3F)]. In the next step [step 3G)] the temperature is increased from about −20 to about 5 °C at a rate between 0.06 and 0.1° C./min (e.g. 0.08 °C/min) and held at that temperature for a desired time [step 3H)]. According to a preferred embodiment, the stage 3) comprises reducing the pressure in the freeze drying chamber to a pressure in a range from about 120 to about 70 mTorr.

Preferably, the pressure in the freeze drying chamber is further reduced to a pressure below atmospheric pressure subsequently to the freezing of the liquid mixture provided in stage 1). In a preferred embodiment, the pressure in the freeze drying chamber is reduced to a pressure below atmospheric pressure before or at the beginning of the drying process. Most preferably, the pressure is reduced before the temperature is increased.

The drying temperature is preferably below the collapse temperature of the frozen mixture obtained in stage 2). More preferably, the drying temperature in stage 3) is below the glass transition temperature of the frozen mixture obtained in stage 2). In specific embodiments, the drying temperature is in a range from about −70 to about 10 °C, preferably from about −60 to about 5 °C. The overall drying rate from the freezing temperature to the final drying temperature is preferably in a range from 0.05 to 1.2 °C/min.

The method of the invention further comprises stage 4) of secondary drying, which comprises further reducing the pressure in the freeze drying chamber to a pressure below atmospheric pressure [step 4A)] of about 35 mTorr while simultaneously increasing the temperature from 5 to 25 °C at the rate of between 0.05 and 0.09 °C/min. Then holding it for a desired time [step 4B)]. According to a preferred embodiment, the stage 4) comprises further reducing the pressure in the freeze drying chamber to a pressure in a range from about 50 to about 30 mTorr.

The method of the invention further comprises stage 4), which comprises further reducing the pressure in the freeze drying chamber to a pressure below atmospheric pressure and increasing the temperature up to room temperature. Preferably, the pressure in the freeze drying chamber is further reduced to a pressure below atmospheric pressure subsequently to the drying of the frozen mixture provided in stage 3). In a preferred embodiment, the pressure in the freeze drying chamber is further reduced to a pressure below atmospheric pressure before or at the beginning of the secondary drying process. Most preferably, the pressure is reduced before the temperature is increased.

The method of the invention further comprises stage 5) in which said glass vial closure and vacuum break with nitrogen is achieved at room temperate and said vial is recovered.

The cooling and heating rates as well as the pressure changes in stages 2), 3) and 4) have an impact on the quality of the lyophilised formulations and are the essence of the invention disclosed herein to maintain the integrity and/or the biological activity of said mRNA complexed formulations upon lyophilisation. According to a preferred embodiment, the heating rate in stages 2), 3) and 4) of the inventive method is thus preferably in a range from 0.05 to 1.2 °C/min, more preferably in a range from 0.06 to 1.0 °C/min.

In a preferred embodiment, disclosed method comprises at least two drying stages, primary drying stage 3) and secondary drying stage 4). In the primary drying stage 3) free, i.e. unbound, water surrounding the mRNA complexed onto nano-carriers and other components, typically escape from the solution. Subsequently, water being bound on a molecular basis by the mRNA complexes is removed in a secondary drying stage 4) by adding thermal energy. In both cases the hydration sphere around the mRNA complexes is lost. Preferably, the primary drying stage 3) comprises heating the frozen mixture to a primary drying temperature, which is preferably lower than a secondary drying temperature, to which the frozen mixture is heated in the secondary drying stage 4). More preferably, the pressure in the primary drying stage 3) ('primary drying pressure') is higher than the pressure in the secondary drying stage 4) ('secondary drying pressure').

According to a further embodiment, stage 3) comprises reducing the pressure in the freeze drying chamber to a primary drying pressure, which is applied before or concomitantly with the heating from the freezing temperature to the primary drying temperature and which is maintained or reduced during the primary drying stage 3); and subsequently reducing the pressure in the freeze drying chamber to a secondary drying pressure, which is applied before or concomitantly with the heating from the primary drying temperature to the secondary drying temperature and which is maintained during the secondary drying stage 4).

The primary drying step 3) may be carried out at normal pressure of about 760 mTorr, but also be carried out by lowering the pressure to a primary drying pressure. Preferably, the primary drying pressure is in the range from about 760 to about 70 mTorr. In this primary drying stage, pressure is typically controlled through the application of partial vacuum. The vacuum allows speeding up sublimation, making it useful as a careful drying process. This stage is carried out slow to avoid applying much heat and possible alteration or damage to the structure of the complexes in said frozen mixture.

In a preferred embodiment, the primary drying stage comprises adjusting the temperature to the primary drying temperature, which is preferably in the range from about −70 to about 10 °C. As a further alternative, the primary drying stage 3) is carried out at a primary drying temperature and a primary drying pressure as defined above in multiple steps.

Preferably, the temperature is reduced from the freezing temperature to the primary drying temperature at a defined cooling rate. More preferably, the temperature is increased in two steps of primary drying [step 3C) and 3E)], preferably from the freezing temperature to the primary drying temperature, at a cooling rate in the range from 0.04 to 0.09 °C/min, more preferably at about 0.07 °C/min. While the pressure is reduced in two steps of primary drying [step 3A) and 3E)], from about 760 to about 100 mTorr and then from about 100 to about 35 mTorr. One embodiment of the cooling and heating cycles as well as the temperature and pressure holds are shown in TABLE 2 as an illustration.

The secondary drying stage 4) typically removes unfrozen water molecules bound to the mRNA complexes, since the ice is usually removed in the primary drying step 3) above. In this secondary drying stage 4), the temperature is typically raised higher than in the primary drying stage 3) to about 25 °C, to break any physico-chemical interactions that have formed between the water molecules and the frozen mixture. Additionally, the pressure may be lowered in this stage to encourage desorption.

In a preferred embodiment, the secondary drying stage 4) comprises adjusting the temperature to a secondary drying temperature and/or adjusting the pressure to a secondary drying pressure. In a specific embodiment, the secondary drying temperature is above the primary drying temperature and/or the secondary drying pressure is below the primary drying pressure. More preferably, the secondary drying temperature is in the range from about 5 to about 25 °C. The pressure is preferably adjusted to the secondary drying pressure. Said secondary drying pressure is preferably in the range from about 30 to about 50 mTorr.

After completion of stage 4) of the inventive method, a lyophilised formulation is typically obtained that comprises at least one mRNA adsorbed onto lipid nano-emulsion particles or nano-carriers and the at least one lyoprotectant.

In a preferred embodiment, subsequent to stage 4), the glass vial is closed with rubber stopper and the freeze drying chamber is flooded with nitrogen or carbon dioxide gas. The glass vial containing the lyophilised formulation, which is obtained according to the inventive method, is closed before the freeze drying chamber is opened by equilibrating it to atmospheric pressure.

The lyophilised formulation obtained by the inventive method is particularly stable for several months at about 5 °C. The storage stability of the mRNA is typically determined through determination of the relative (structural) integrity and the biological activity after a given storage period.

Figure 4:
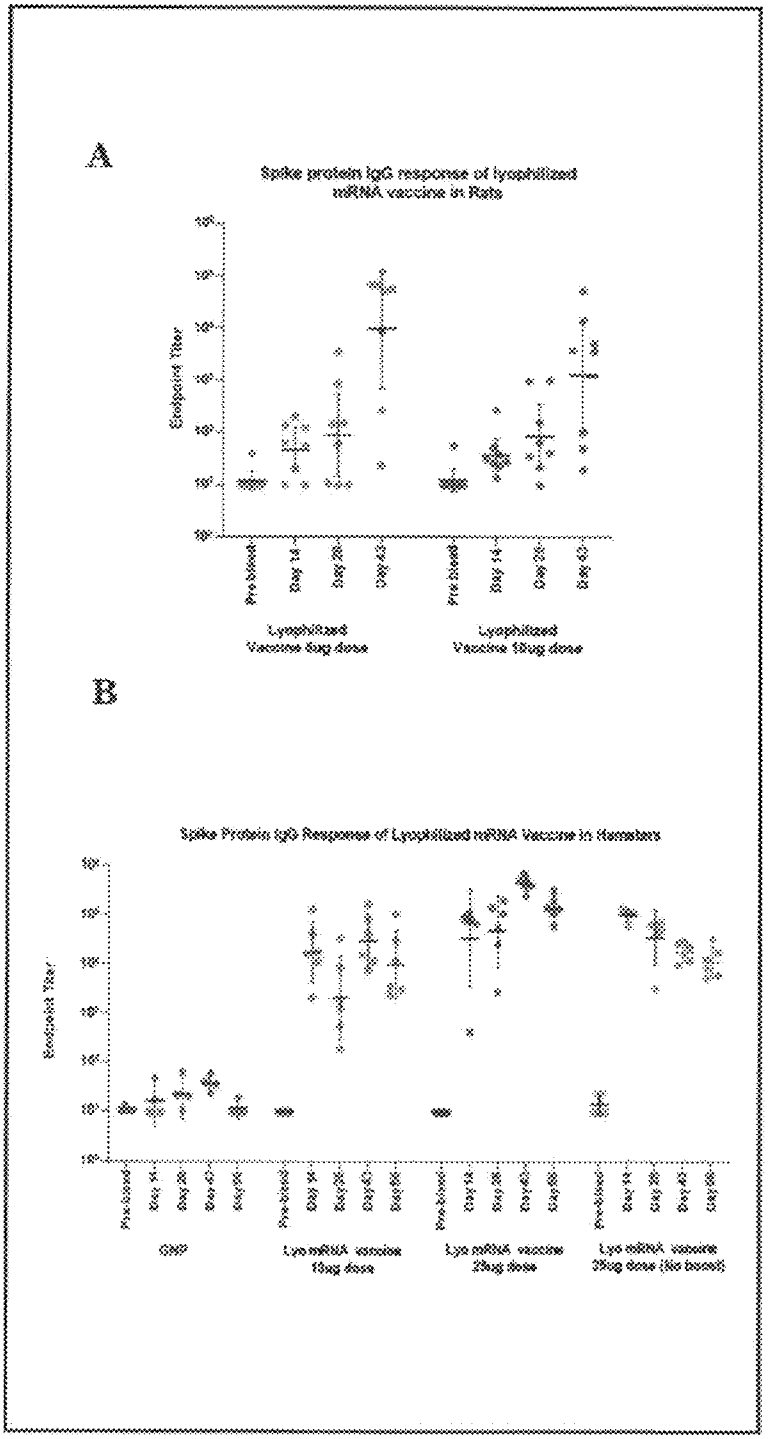
Figure 5:
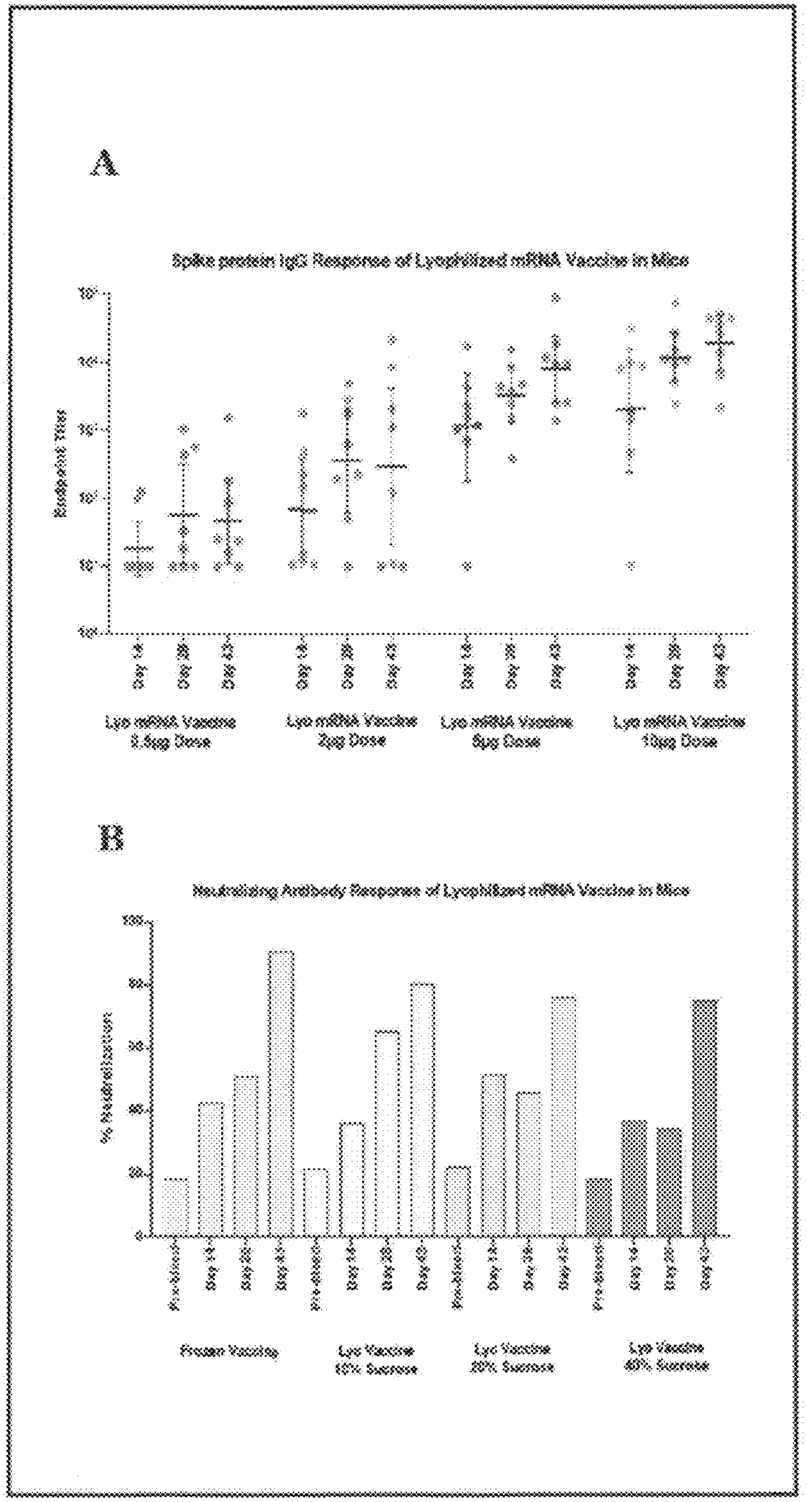

The storage stability of the lyophilised formulations is described in TABLES 5, 6 and 7. Briefly, the lyophilised formulations with 10, 20 or 40 percent sucrose, Formulation A, B and C, respectively, were subjected to various bioanalytical tests at five time points upon storage of said formulations at Day Zero up to Month 9 at about 5 °C. The physico-chemical properties of the formulations of the mRNA adsorbed onto lipid nano-emulsion particles or nano-carriers were tested as shown in TABLES 5, 6 and 7; and FIGS. 1, 2 and 3. The four important parameters, the particle size, dispersity and mRNA content and immunogenicity (IgG titre in mouse tests) of the formulations were compared amongst others. The lyophilised formulation containing about 20% sucrose as a lyoprotecant showed desired results with the stability of several parameters over a period of about nine months. There were negligible differences between these parameters when compared with Day Zero and Month 9 of storage at about 5 °C. The integrity of the mRNA molecules of said formulation was intact and it showed good immunogenic properties when tested in rat and hamster models with production of sufficient IgG antibodies against the SARS-COV-2 spike protein. The TABLES 5, 6 and 7 and FIGS. 1, 2 and 3 describe the properties of various lyophilised formulations prepared by the inventive method disclosed herein. FIGS. 4 and 5 describes immunogenicity properties of the said lyophilised formulations.

The lyophilised formulation obtainable by the inventive method allows significantly longer storage at temperatures of about 5 °C than the corresponding mRNA molecules in WFI or other injectable solutions. Particularly, the lyophilised formulation obtained by the inventive method can be stored at room temperature, which simplifies shipping and storage processes.

Preferably, the relative integrity of the mRNA in the lyophilised formulation obtained by the inventive method is at least 70%, more preferably at least 90% after storage at temperature of about 5 °C for preferably at least for three months, more preferably at least for 6 months and most preferably at least for one year.

Further preferably, the biological activity of the mRNA of the lyophilised formulation after storage at temperature of about 5 °C, preferably as defined above with respect to the relative integrity of the mRNA, is preferably at least 70%, more preferably at least 90% of the biological activity of the freshly prepared mRNA. The biological activity is preferably determined by analysis of the amounts of protein expressed from reconstituted mRNA complexed to said nano-carriers and from freshly prepared mRNA, respectively, e.g. after transfection into a mammalian cell line or into a subject. Alternatively, the biological activity may be determined by measuring the induction of an immune response in a subject.

In a preferred embodiment, said lipid nano-emulsion particles or nano-carriers comprise a cationic lipid like DOTAP (1,2-dioleoyl-3-trimethylammonium-propane), a liquid lipid like squalene, a hydrophobic surfactant like sorbitan monostearate, a hydrophilic surfactant like polysorbate-80 and self-replicating mRNA molecules capable of expressing SARS-COV2 spike protein mutants or variants.

In a further aspect, the present invention further provides the use of the inventive method in the manufacture of a pharmaceutical preparation or said lyophilised formulation may be used directly as a pharmaceutical product.

Furthermore, the inventive lyophilised formulation disclosed herein may comprise a pharmaceutically acceptable carrier and/or vehicle. In the context of the present invention, a pharmaceutically acceptable carrier typically includes the liquid or non-liquid basis of the inventive pharmaceutical lyophilised formulation.

FIGURES

The figures shown in the following are merely illustrative and shall describe the present invention in a further way. These figures shall not be construed to limit the present invention thereto.

FIG. 1: Shows integrity of mRNA after adsorption onto lipid nano-emulsion particles or nano-carriers present in the lyophilised formulations at Day Zero after lyophilisation process on the electrophoresis image. Lane 1 is the RNA molecular weight marker having first band of 9 kb, sixth band of 3 kb and tenth band of 0.5 kb of single strand RNA transcripts. Lane 2 is of about 12 kb of purified self-replicating SARS-COV-2 S-protein expressing mRNA molecules. Lane 5 is the liquid formulation with 10% sucrose, where RNA is mRNA bound to the nano-carriers immobilised in the well. Lane 6 is same liquid formulation with 20% sucrose. Lane 7 is same liquid formulation with 40% sucrose. Samples of Lanes from 5 to 7 were kept at about 25 °C. Lane 9 is the lyophilised formulation with 10% sucrose, where RNA is mRNA bound to the nano-carriers immobilised in the well. Lane 10 is same lyophilised formulation with 20% sucrose. Lane 11 is same lyophilised formulation with 40% sucrose. Lane 13 is the mRNA solvent extracted from the lyophilised formulation with 10% sucrose, where RNA is mRNA migrated from the well to the location at about 12 kb. Lane 14 is same extracted formulation with 20% sucrose. Lane 15 is same extracted formulation with 40% sucrose. Samples of Lanes from 9 to 11 and from 13 to 15 were stored at about 5 °C before use. Lane 17 is the lyophilised formulation with 10% sucrose, where RNA is mRNA bound to the nano-carriers immobilised in the well. Lane 18 is same lyophilised formulation with 20% sucrose. Lane 19 is same lyophilised formulation with 40% sucrose. Lane 21 is the mRNA solvent extracted from the lyophilised formulation with 10% sucrose, where RNA is mRNA migrated from the well to the location at about 12 kb. Lane 22 is same extracted formulation with 20% sucrose. Lane 23 is same extracted formulation with 40% sucrose. Samples of Lanes from 17 to 19 and from 21 to 23 were stored at about 25 °C before use. Lane 25 is extracted liquid formulation with 10% sucrose as a control. In all the formulations the nano-carrier used is GNP type with a self-replicating SARS-COV-2 S-protein coding mRNA expressed in-vitro from a plasmid template.

Figure 2:
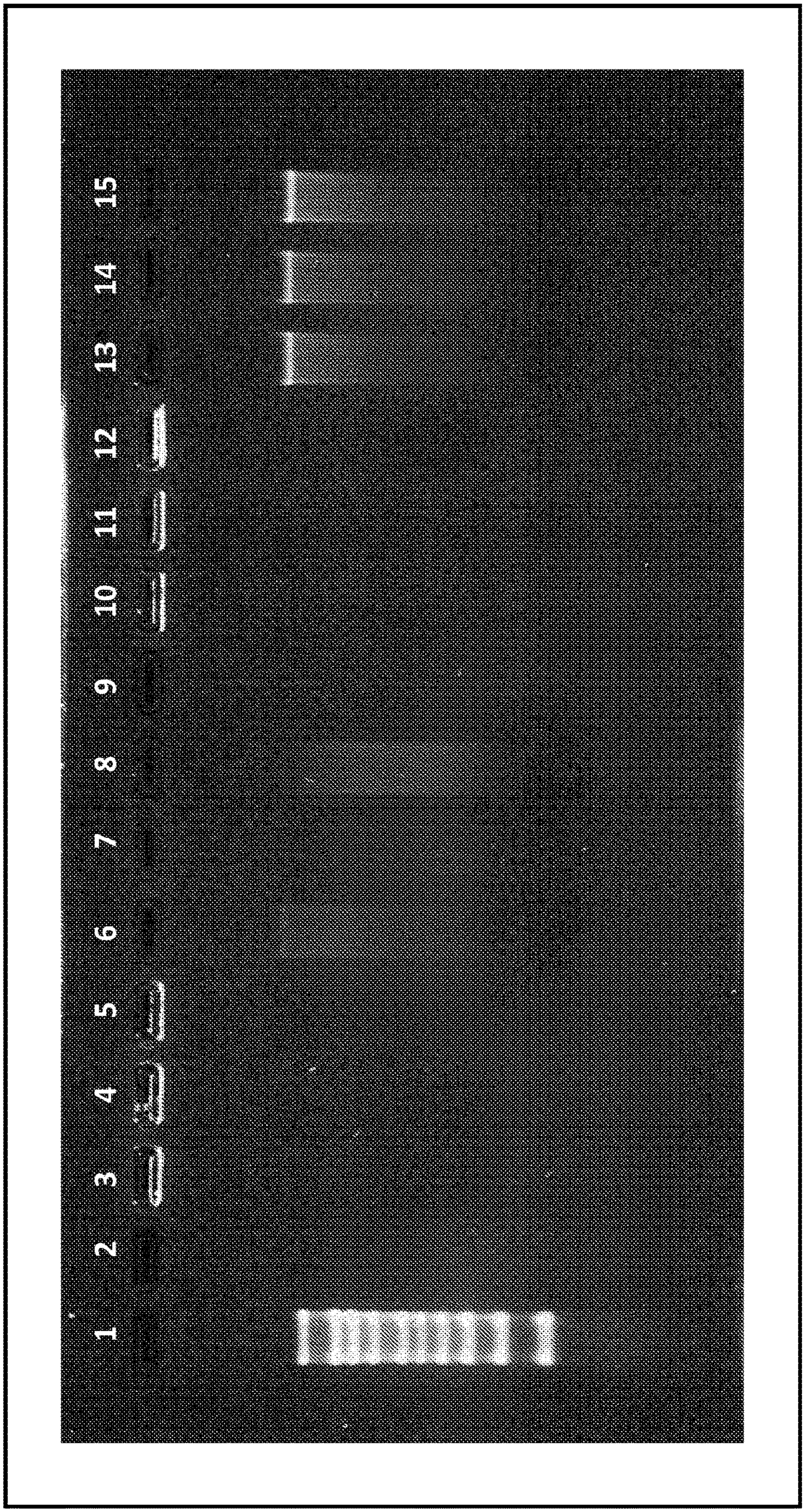

FIG. 2: Shows integrity of mRNA after adsorption onto lipid nano-emulsion particles or nano-carriers present in the lyophilised formulations at Day 90 after lyophilisation process on the electrophoresis image. Lane 1 is the RNA molecular weight marker having first band of 9 kb, sixth band of 3 kb and tenth band of 0.5 kb of single strand RNA transcripts. Lane 3 is the lyophilised formulation with 10% sucrose, where RNA is mRNA bound to the nano-carriers immobilised in the well. Lane 4 is same lyophilised formulation with 20% sucrose. Lane 5 is same lyophilised formulation with 40% sucrose. Lane 6 is the mRNA solvent extracted from the lyophilised formulation with 10% sucrose, where RNA is mRNA migrated from the well to the location at about 12 kb. Lane 7 is same extracted formulation with 20% sucrose. Lane 8 is same extracted formulation with 40% sucrose. Samples of Lanes from 3 to 8 were stored at about 25 °C before use for 90 days. Lane 10 is the lyophilised formulation with 10% sucrose, where RNA is mRNA bound to the nano-carriers immobilised in the well. Lane 11 is same lyophilised formulation with 20% sucrose. Lane 12 is same lyophilised formulation with 40% sucrose. Lane 13 is the mRNA solvent extracted from the lyophilised formulation with 10% sucrose, where RNA is mRNA migrated from the well to the location at about 12 kb. Lane 14 is same extracted formulation with 20% sucrose. Lane 15 is same extracted formulation with 40% sucrose. Samples of Lanes from 10 to 15 were stored at about 5 °C before use for 90 days. In all the formulations the nano-carrier used is GNP type with a self-replicating SARS-COV-2 S-protein coding mRNA expressed in-vitro from a plasmid template.

Figure 3:
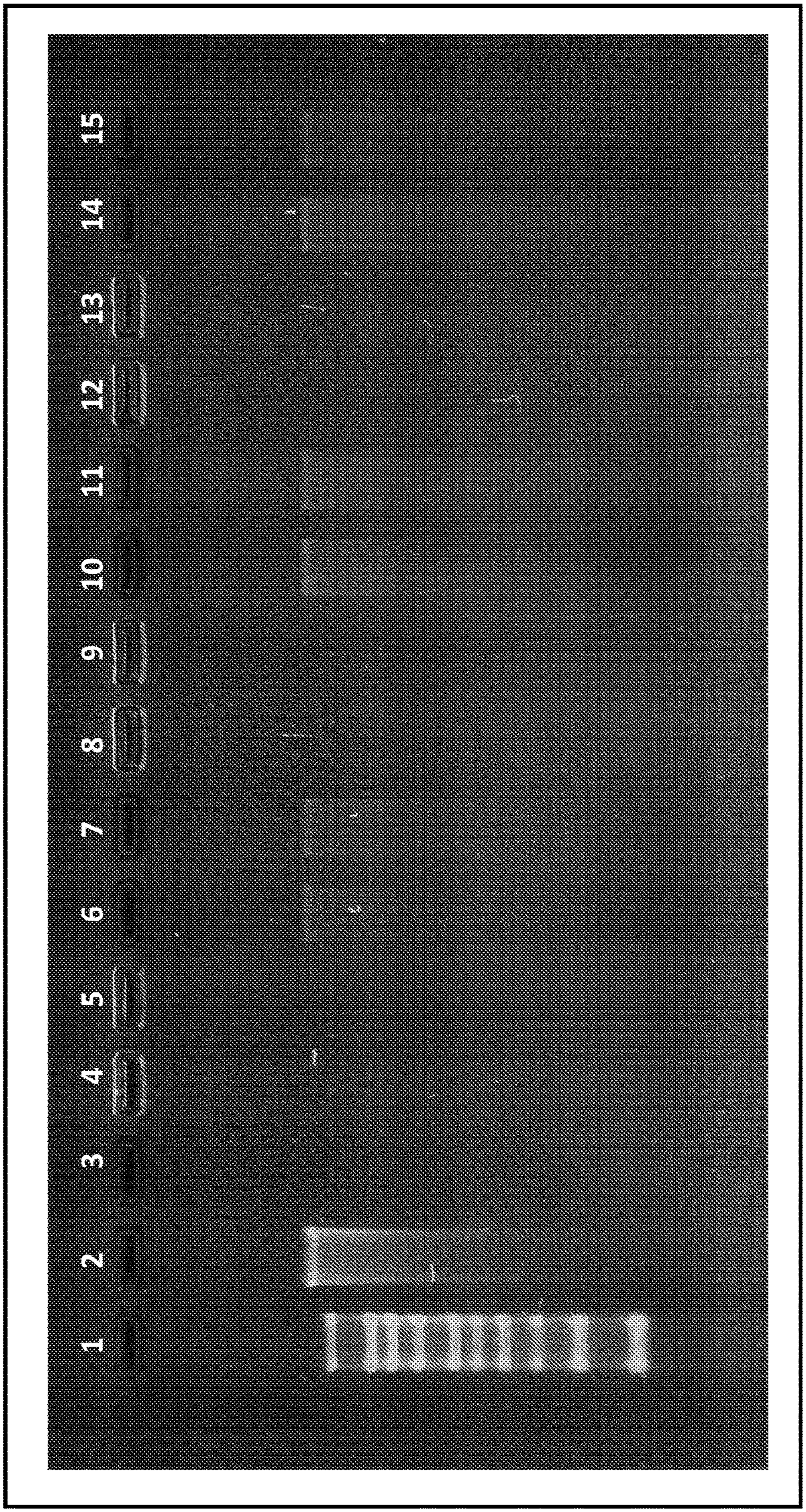

FIG. 3: Shows the integrity of mRNA in the lyophilised formulations treated with RNAse at the end of nine-month period of storage at about 5 °C on the electrophoresis image. Lane 1 is the RNA molecular weight marker having the first band of 9 kb, sixth band of 3 kb and tenth band of 0.5 kb of single strand RNA transcripts. Lane 2 is of about 12 kb of purified self-replicating SARS-COV-2 S-protein expressing mRNA molecules untreated by RNase. Lane 3 is of the same mRNA molecules treated by RNase get degraded. Lane 4 is said Formulation A untreated. Lane 5 is said Formulation A treated. Lane 6 is mRNA extracted from said Formulation A untreated. Lane 7 is mRNA extracted from said Formulation A treated. Lane 8 is said Formulation B untreated. Lane 9 is said Formulation B treated. Lane 10 is mRNA extracted from said Formulation B untreated. Lane 11 is mRNA extracted from said Formulation B treated. Lane 12 is said Formulation C untreated. Lane 13 is said Formulation C treated. Lane 14 is mRNA extracted from said Formulation C untreated. Lane 15 is mRNA extracted from said Formulation C treated.

FIG. 4: Shows the immune response generated by vaccine Formulation B comprising the mRNA molecules and nano-carriers of the invention disclosed herein. The SARS-COV-2 spike protein producing self-replicating mRNA constructs when adsorbed onto the nano-carriers, called GNP, and injected into rats and hamsters produced robust IgG responses.

FIG. 5: Shows the immune response generated by different vaccine formulations comprising the mRNA molecules and nano-carriers of the invention disclosed herein. The SARS-COV-2 spike protein producing self-replicating mRNA constructs when adsorbed onto the nano-carriers, called GNP, and injected into mice produced robust IgG responses as well as surrogate virus neutralising antibodies.

EXAMPLES

The Examples shown below are illustrative, further describing the present invention and shall not be construed to limit it.

Example 1: Preparation of mRNA Adsorbed onto Lipid Nano-Emulsion Particles in Liquid A process for the preparation of self-replicating mRNA constructs and of mRNAs capable of expressing SARS-COV-2 spike protein antigens [COVID-19 S Protein Antigen] and other similar antigens has been previously disclosed by the inventors. Similarly, a process for the preparation of the lipid nano-emulsion particles or nano-carriers [also called GNPs herein] has been previously disclosed by the inventors. Briefly, said mRNA adsorbed onto nano-carriers in liquid comprises a cationic lipid like DOTAP (1,2-dioleoyl-3-trimethylammonium-propane), a liquid lipid like squalene, a hydrophobic surfactant like sorbitan monostearate, a hydrophilic surfactant like polysorbate-80 and self-replicating mRNA molecules of interest [e.g., expressing SARS-COV2 spike protein mutants] in a buffer like citrate buffer forming liquid formulations used for the lyophilisation methods disclosed herein. The said nano-carriers or GNPs optionally also contain immunostimulant compounds like toll-like receptor 4 antagonist adjuvants like monophosphoryl lipid-A [MPL] or glucopyranosyl lipid-A [GLA] compounds.

Example 2: Preparation and Properties of Liquid Formulations

The preparation of the nano-carriers or GNPs was achieved in a three-part process. In first part, the oil phase was prepared using all the hydrophobic substances that form the part of the said carrier. Herein, to prepare about 5 mL of said oil phase, about 3 g of DOTAP, about 3.7 g of sorbitan monostearate and about 3.75 g of squalene were mixed in a glass container. Said mixture was warmed at about 65 °C till all the components got well mixed in homogenous consistency. In second part, about 3.7 g of polysorbate-80 was mixed with 90 mL of 10 mM sodium citrate, pH 6.0 buffered solution, which was kept warm at 65° C. In third part, both the oil and aqueous phases were mixed under high shear mixer running at about 5000 RPM for about 15 minutes. Then this mixture was passed about 10 times through high pressure homogenizer at about 30,000 psi and primed with remaining aqueous phase affording about 100 mL of nano-carrier solution. The said nano-carrier solution optionally contained immunostimulating substances like MPL or GLA at an amount of about 0.5 μg/mL when desired. The nano-carrier GNP contained no MPL or GLA, while GNP-M contained MPL adjuvant and GNP-G contained GLA adjuvant [see TABLE 1].

The adsorption of mRNA molecules onto said nano-carrier was performed with a very careful and precise process of mixing of said nano-carrier solution into said mRNA solution forming the stable complexes. Herein, the ratio of nitrogen [present on the DOTAP molecules] to phosphate [present on the RNA molecules; N:P ratio] was taken as a measure of association of said mRNA molecules to said nano-carrier particles as the mRNA molecules being negatively charged while the DOTAP molecules being positively charged, leading to adsorption of said mRNA molecules on said nano-carriers. To achieve the stable complexes of mRNA molecules with nano-carriers various N: P ratios between 1 and 150 of DOTAP to mRNA amounts were tried, keeping the amount of mRNA constant. This led to the N:P ratios between 5 and 15 as ideal for obtaining the stable complexes of the mRNA adsorbed onto said nano-carriers. Therefore, to prepare said complexes, the said nano-carrier solution above described is diluted to about 6 mg/mL of DOTAP with 10 mM sodium citrate, pH 6.0 solution containing about 200 mg/mL of sucrose. Then, about 50 mL of this diluted nano-carrier solution was taken in a 1000-mL container and placed on a shaker rotating at about 180 RPM. Then about 50 mL of mRNA solution as prepared in Example 3 was added slowly using a syringe pump in about 10 minutes under the constant stirring condition at temperature of about 5 °C. Then the mixture was allowed to form complexes at 5 °C for about 30 minutes and then the said complex solution was filtered through 0.45 μm and 0.22 μm membrane filters to obtain the sterile vaccine solution. To determine the amount of RNA molecules adsorbed onto the nano-carrier particles and changes in the properties of said nano-carrier, average particle sizes and particle size distribution parameters were measured by dynamic light scattering on Zetasizer Nano ZS system [Malvern Panalytical]. TABLE 1 provides changes observed in said parameters of the nano-carriers upon adsorption of mRNA molecules.

TABLE 1

| S/N | PARAMETER | GNP | GNP-M | GNP-G | GNP + mRNA | GNP-M + mRNA | GNP-G + mRNA |
|---|---|---|---|---|---|---|---|
| 1 | Particle size [nm] | 51.00 | 40.71 | 50.50 | 63.34 | 56.98 | 72.28 |
| 2 | PDI | 0.271 | 0.196 | 0.184 | 0.224 | 0.207 | 0.180 |
| 3 | Zeta potential [mV] | 34.8 | 28.3 | 33.2 | 11.1 | 11.4 | 10.5 |
| 4 | RNA content [μg/mL] | — | — | — | 40.70 | 44.80 | 40.40 |
| 5 | Binding Efficiency [%] | — | — | — | 98.30 | 98.10 | 89.90 |

Example 3: Freeze Drying Process and Parameter Optimization

A general scheme of the freeze drying cycle for the lyophilisation of complex drug formulations like the one herein disclosed is depicted in TABLE 2. Briefly, it comprises five stages with varying temperature and pressure steps that effectively aid in the freeze drying of said liquid formulations of mRNA adsorbed onto lipid nano-emulsion particles or nano-carriers to lyophilised formulations that are stable for at least six months at temperature of about 5 °C. In the early experiments a freeze drying cycle with 5-day process cycle was used to lyophilise the liquid formulations used herein. On the establishment of the workability of the said lyophilisation process with desired results further reduction in the process cycle to 3-day cycles was achieved as depicted in TABLES 3 to 4A.

TABLE 2

One embodiment of freeze drying cycle of the disclosed invention with 5-day process cycle.

| STAGE | STEP | ACTION | SHELF TEMP CHANGE [° C.] | COOLING/HEATING RATE [° C./min] | PRESSURE [mTorr] | TIME [min] |
|---|---|---|---|---|---|---|
| 1 | A | Loading Pre-cooling | 25 to 5 | 0.94 | 760 | 20 |
| 2 | A | Freezing | 5 to −60 | 0.94 | 760 | 70 |
| | B | | −60 | — | 760 | 300 |
| 3 | A | Primary drying | −60 | — | 760 to 112 | 30 |
| | B | | −60 | — | 112 | 1440 |
| | C | | −60 to −40 | 0.07 | 112 | 300 |
| | D | | −40 | — | 112 | 1200 |
| | E | | −40 to −20 | 0.07 | 112 to 75 | 300 |
| | F | | −20 | — | 75 | 1200 |
| | G | | −20 to 5 | 0.08 | 75 | 300 |
| | H | | 5 | — | 75 | 1200 |
| 4 | A | Secondary drying | 5 to 25 | 0.07 | 75 to 37 | 300 |
| | B | | 25 | — | 37 | 540 |
| 5 | A | Vial closure | 25 | — | 37 | 05 |
| | B | Vacuum break with $N_2$ | 25 | — | 37 to 760 | 10 |

TABLE 3

One embodiment of freeze drying cycle of the disclosed invention with 3-day process cycle.

| STAGE | STEP | ACTION | SHELF TEMP CHANGE [° C.] | COOLING/HEATING RATE [° C./min] | PRESSURE [mTorr] | TIME [min] |
|---|---|---|---|---|---|---|
| 1 | A | Loading Pre-cooling | 5 | — | 760 | 10 |
| 2 | A | Freezing | 5 to −5 | 0.5 | 760 | 20 |
| | B | | −5 | — | 760 | 30 |
| | C | | −5 to −45 | 0.5 | 760 | 80 |
| | D | | −45 | — | 760 | 600 |
| 3 | A | Primary drying | −45 | — | 760 to 200 | 10 |
| | B | | −45 to −40 | 0.1 | 200 to 60 | 50 |
| | C | | −40 | — | 60 | 180 |
| | D | | −40 to −35 | 0.1 | 60 to 50 | 50 |
| | E | | −35 | — | 50 | 400 |
| | F | | −35 to −30 | 0.1 | 50 | 50 |
| | G | | −30 | — | 50 | 600 |
| | H | | −30 to −25 | 0.1 | 50 | 50 |
| | I | | −25 | — | 50 | 450 |
| | J | | −25 to −20 | 0.1 | 50 | 50 |
| | K | | −20 | — | 50 | 300 |
| | L | | −20 to 0 | 0.07 | 50 | 100 |
| | M | | 0 | — | 50 | 200 |
| | N | | 0 to 10 | 0.1 | 50 | 100 |
| | O | | 10 | — | 50 | 400 |
| 4 | A | Secondary drying | 10 to 25 | 0.15 | 50 | 100 |
| | B | | 25 | — | 50 | 600 |
| 5 | A | Vial Closure | 10 | — | 50 | 05 |
| | B | Vacuum break with $N_2$ | 10 | — | 760 | 10 |

TABLE 4

One embodiment of freeze drying cycle of the disclosed invention with another 3-day process cycle.

| STAGE | STEP | ACTION | SHELF TEMP CHANGE [° C.] | COOLING/HEATING RATE [° C./min] | PRESSURE [mTorr] | TIME [min] |
|---|---|---|---|---|---|---|
| 1 | A | Loading Pre-cooling | 25 | — | 760 | 10 |
| 2 | A | Freezing | 25 to −55 | 0.67 | 760 | 120 |
| | B | | −55 | — | 760 | 420 |
| 3 | C | Primary drying | −55 | — | 760 to 112 | 180 |
| | D | | −55 to −40 | 0.08 | 112 | 180 |
| | E | | −40 | — | 112 | 300 |
| | F | | −40 to −35 | 0.08 | 112 | 60 |
| | G | | −35 | — | 112 | 360 |
| | H | | −35 to −30 | 0.08 | 75 | 60 |
| | I | | −30 | — | 75 | 480 |
| | J | | −30 to −20 | 0.03 | 75 | 300 |
| | K | | −20 | — | 75 | 480 |
| | L | | −20 to −5 | 0.05 | 75 | 300 |

TABLE 4-continued

One embodiment of freeze drying cycle of the disclosed invention with another 3-day process cycle.

| STAGE | STEP | ACTION | SHELF TEMP CHANGE [° C.] | COOLING/HEATING RATE [° C./min] | PRESSURE [mTorr] | TIME [min] |
|---|---|---|---|---|---|---|
| | M | | −5 | — | 75 | 300 |
| | N | | −5 to 5 | 0.08 | 37 | 120 |
| | O | | 5 | — | 37 | 300 |
| 4 | A | Secondary drying | 5 to 25 | 0.16 | 37 | 120 |
| | B | | 25 | — | 37 | 360 |
| 5 | A | Vial Closure | 25 | — | 37 | 05 |
| | B | Vacuum break with $N_2$ | 25 | — | 760 | 10 |

TABLE 4A

One embodiment of freeze drying cycle of the disclosed invention with 2-day process cycle.

| STAGE | STEP | ACTION | SHELF TEMP CHANGE [° C.] | COOLING/HEATING RATE [° C./min] | PRESSURE [mTorr] | TIME [min] |
|---|---|---|---|---|---|---|
| 1 | A | Loading Pre-cooling | 25 | — | 760 | 10 |
| 2 | A | Freezing | 25 to −55 | 0.67 | 760 | 120 |
| | B | | −55 | — | 760 | 300 |
| 3 | C | Primary drying | −55 | — | 760 to 112 | 60 |
| | D | | −55 to −40 | 0.25 | 112 | 60 |
| | E | | −40 | — | 112 | 240 |
| | F | | −40 to −35 | 0.08 | 112 | 60 |
| | G | | −35 | — | 112 | 300 |
| | H | | −35 to −30 | 0.08 | 75 | 60 |
| | I | | −30 | — | 75 | 300 |
| | J | | −30 to −20 | 0.04 | 75 | 240 |
| | K | | −20 | — | 75 | 300 |
| | L | | −20 to −5 | 0.08 | 75 | 180 |
| | M | | −5 | — | 75 | 180 |
| | N | | −5 to 5 | 0.08 | 37 | 120 |
| | O | | 5 | — | 37 | 180 |
| 4 | A | Secondary drying | 5 to 25 | 0.33 | 37 | 60 |
| | B | | 25 | — | 37 | 240 |
| 5 | A | Vial Closure | 25 | — | 37 | 05 |
| | B | Vacuum break with $N_2$ | 25 | — | 760 | 10 |

Example 4: Long-Term Stability and Functional Properties of Lyophilised mRNA Formulations To determine the effect of long-term storage on the lyophilised formulations of mRNA adsorbed onto the lipid nano-emulsion particles or nano-carriers, the said lyophilised formulations containing sucrose at about 10% [Formulation A, see TABLE 5], 20% [Formulation B, see TABLE 6] or 40% [Formulation C, see TABLE 7] were stored at about 5 °C up to nine months and tested for several physico-chemical parameters as listed in TABLES 5, 6 and 7. Further, the said formulations were subjected to RNase protection assays to assess the integrity of the mRNA molecules present in said formulations [see FIGS. 1 to 3]. This data shows the integrity and stability of the said formulations of the vaccine under the disclosed storage conditions. The said vaccine formulations comprise mRNA transcript capable of expressing full-length SAR-COV-2 spike protein at an amount between 5 and 300 µg/mL. Beside other components of the vaccine formulations comprise: DOTAP at an amount between 0.2 and 1.0 mg/mL; squalene at an amount between 0.2 and 1.0 mg/mL; sorbitan monostearate at an amount between 0.2 and 1.0 mg/mL; polysorbate-80 at an amount between 0.2 and 1.0 mg/ml; and citric acid monohydrate at an amount between 0.2 and 1.0 mg/mL.

TABLE 5

FORMULATION A

| | | | Day | Month | | | |
|---|---|---|---|---|---|---|---|
| S/N | Test | Acceptance Criteria | Zero | One | Three | Six | Nine |
| 1. | Appearance of Cake | Off-white amorphous intact cake with uniform appearance. | | | Complies | | |
| 2. | Appearance after Reconstitution | Translucent liquid free of any visible particles. | | | Complies | | |
| 3. | Reconstitution Time [Second] | NMT 180 | 150 | 140 | 150 | 155 | 150 |
| 4. | pH | 6.0 ± 0.5 | 6.13 | 6.20 | 6.25 | 6.20 | 6.30 |
| 5. | Particle Size [nm] | 70 to 150 | 107 | 106 | 109 | 104 | 118 |
| 6. | Polydispersity Index | 0.2 to 0.4 | 0.26 | 0.26 | 0.28 | 0.28 | 0.28 |
| 7. | RNA Integrity in Complex by Agarose Gel Electrophoresis | Free RNA should not be detected in the gel below the loading well. | | | Complies | | |

TABLE 5-continued

| FORMULATION A | | | | | | | |
|---|---|---|---|---|---|---|---|
| | | | Day | Month | | | |
| S/N | Test | Acceptance Criteria | Zero | One | Three | Six | Nine |
| 8. | RNase Protection by Agarose Gel Electrophoresis | The size of extracted RNA from RNase treated sample and the extracted RNA from untreated sample should be above 9 kb marker. | | | Complies | | |
| 9. | Extracted mRNA Recovery by Fluorescence Assay [μg/mL] | 16 to 24 | 20.4 | 21.6 | 19.8 | 21.2 | 23.3 |
| 10. | DOTAP Content by RP-HPLC [mg/mL] | 0.48 to 0.72 | 0.67 | 0.55 | 0.62 | 0.57 | 0.57 |
| 11. | Squalene Content by RP-HPLC [mg/mL] | 0.6 to 0.9 | 0.68 | 0.71 | 0.75 | 0.79 | 0.78 |
| 12. | Osmolality [mOsm/kg] | 250 to 400 | 292 | 295 | 294 | 299 | 280 |
| 13. | Moisture Content [%] | NMT 5 | 3.40 | 3.57 | 3.57 | 3.73 | 4.11 |

TABLE 6

| FORMULATION B | | | | | | | |
|---|---|---|---|---|---|---|---|
| | | | Day | Month | | | |
| S/N | Test | Acceptance Criteria | Zero | One | Three | Six | Nine |
| 1. | Appearance of Cake | Off-white amorphous intact cake with uniform appearance. | | | Complies | | |
| 2. | Appearance after Reconstitution | Translucent liquid free of any visible particles. | | | Complies | | |
| 3. | Reconstitution Time [Second] | NMT 180 | 140 | 130 | 145 | 150 | 150 |
| 4. | pH | 6.0 ± 0.5 | 6.10 | 6.18 | 6.20 | 6.19 | 6.17 |
| 5. | Particle Size [nm] | 70 to 150 | 103 | 103 | 108 | 107 | 101 |
| 6. | Polydispersity Index | 0.2 to 0.4 | 0.26 | 0.25 | 0.25 | 0.26 | 0.25 |
| 7. | RNA Integrity in Complex by Agarose Gel Electrophoresis | Free RNA should not be detected in the gel below the loading well. | | | Complies | | |
| 8. | RNase Protection by Agarose Gel Electrophoresis | The size of extracted RNA from RNase treated sample and the extracted RNA from untreated sample should be above 9 kb marker. | | | Complies | | |
| 9. | Extracted mRNA Recovery by Fluorescence Assay [μg/mL] | 16 to 24 | 22.3 | 22.0 | 21.9 | 22.1 | 21.5 |
| 10. | DOTAP Content by RP-HPLC [mg/mL] | 0.48 to 0.72 | 0.66 | 0.57 | 0.63 | 0.61 | 0.56 |
| 11. | Squalene Content by RP-HPLC [mg/mL] | 0.6 to 0.9 | 0.68 | 0.68 | 0.68 | 0.73 | 0.75 |
| 12. | Osmolality [mOsm/kg] | 250 to 400 | 289 | 288 | 295 | 304 | 293 |
| 13. | Moisture Content [%] | NMT 5 | 3.45 | 3.51 | 3.68 | 3.26 | 3.81 |

TABLE 7

| FORMULATION C | | | | | | | |
|---|---|---|---|---|---|---|---|
| | | | Day | Month | | | |
| S/N | Test | Acceptance Criteria | Zero | One | Three | Six | Nine |
| 1. | Appearance of Cake | Off-white amorphous intact cake with uniform appearance. | | | Complies | | |
| 2. | Appearance after Reconstitution | Translucent liquid free of any visible particles. | | | Complies | | |
| 3. | Reconstitution Time [Second] | NMT 180 | 140 | 130 | 145 | 150 | 140 |
| 4. | pH | 6.0 ± 0.5 | 6.10 | 6.18 | 6.20 | 6.19 | 6.21 |
| 5. | Particle Size [nm] | 70 to 150 | 101 | 102 | 106 | 104 | 105 |
| 6. | Polydispersity Index | 0.2 to 0.4 | 0.24 | 0.26 | 0.26 | 0.24 | 0.26 |
| 7. | RNA Integrity in Complex by Agarose Gel Electrophoresis | Free RNA should not be detected in the gel below the loading well. | | | Complies | | |
| 8. | RNase Protection by Agarose Gel Electrophoresis | The size of extracted RNA from RNase treated sample and the extracted RNA from untreated sample should be above 9 kb marker. | | | Complies | | |
| 9. | Extracted mRNA Recovery by Fluorescence Assay [μg/mL] | 16 to 24 | 21.8 | 19.8 | 21.8 | 19.3 | 20.5 |
| 10. | DOTAP Content by RP-HPLC [mg/mL] | 0.48 to 0.72 | 0.61 | 0.61 | 0.62 | 0.65 | 0.56 |
| 11. | Squalene Content by RP-HPLC [mg/mL] | 0.6 to 0.9 | 0.70 | 0.71 | 0.71 | 0.75 | 0.75 |

TABLE 7-continued

| FORMULATION C | | | | | | | |
|---|---|---|---|---|---|---|---|
| | | | Day | Month | | | |
| S/N | Test | Acceptance Criteria | Zero | One | Three | Six | Nine |
| 12. | Osmolality [mOsm/kg] | 250 to 400 | 295 | 300 | 290 | 291 | 282 |
| 13. | Moisture Content [%] | NMT 5 | 3.61 | 3.34 | 3.35 | 3.27 | 3.50 |

Example 5: Immunogenicity Studies in Rat and Hamster

The vaccine formulations obtained in Example 3 were subjected to the immunogenicity studies to determine the immunogen-producing properties of the mRNA molecules adsorbed onto said nano-carriers and the immune responses it create. Herein, said vaccine formulations or control were injected into Wistar rats and Syrian hamster populations. The study on Wister rats was conducted on 16 animals, each group consisting of 8 rats. The first group was injected on Day 1 with 100 μL of reconstituted lyophilized vaccine of Formulation B, which had a total mRNA content of 5 μg followed by a booster dose on Day 29 of the same amount. The second group was injected on Day 1 with 100 μL of reconstituted lyophilized vaccine of Formulation B, which had a total mRNA content of 10 μg and was followed by a booster dose on Day 29 of the same amount. Immunogenicity was analyzed at four time points namely pre-bleed (2 days prior to priming injection), Day 14, Day 28 and Day 43. Immunogenicity analysis was performed using standard indirect ELISA methods. An exponential increase in immunogenic response was observed in both groups injected with 5 μg dose and 10 μg dose of lyophilized vaccine respectively [see FIG. 4A]. The study on Syrian hamsters was conducted on 22 animals, with a control group consisting of 4 animals and three test groups having 6 animals. The control group was injected with 100 μL of GNP [nano-carrier only] on Day 1 and followed by a booster dose on Day 29 of the same amount. The first test group was injected on Day 1 with reconstituted lyophilized mRNA vaccine of Formulation B having a total mRNA content of 10 μg and a booster dose on Day 29 of the same amount. The second test group was injected on Day 1 with reconstituted lyophilized mRNA vaccine of Formulation B having a total mRNA content of 25 μg and a booster dose on Day 29 of the same amount. The third test group was injected on Day 1 only with a priming dose of reconstituted lyophilized vaccine of Formulation B having a total mRNA content of 25 μg only and without the booster dose. Immunogenicity was analyzed at five time points namely pre-bleed (2 days prior to priming injection), Day 14, Day 28, Day 43 and Day 56. Immunogenicity analysis was performed using standard indirect ELISA methods. No significant increase in immune response was observed in the control group injected with GNP up to Day 56. All three test groups showed a marked increase in immunogenicity at Day 14 as compared to pre-bleed titers. A slight decrease in immunogenicity was observed in the first test group on Day 28, while the immune response was maintained in second test group. First and second test groups showed a marked increase in immune response on Day 43 which slightly dropped on day 56. The third test group shows a decline in titer from Day 28 up to Day 56. Thus, it is evident that said lyophilized formulation of mRNA vaccine is stable and immunogenic in various animal models [see FIG. 4B].

Example 6: Immunogenicity Studies in Mouse

Immunogenicity of said mRNA vaccine Formulation B was additionally tested in C57BL/6 mouse model. The study was conducted on a group of 32 animals, each group consisting of 8 animals. The first test group was injected on Day 1 with 100 μL of reconstituted lyophilized vaccine Formulation B, which had a total mRNA content of 0.5 μg followed by a booster dose on Day 29 of the same amount. The second test group was injected on Day 1 with 100 μL of reconstituted lyophilized vaccine Formulation B, which had a total mRNA content of 2 μg and was followed by a booster dose on Day 29 of the same amount. The third test group was injected on Day 1 with 100 μL of reconstituted lyophilized vaccine Formulation B, which had a total mRNA content of 5 μg and was followed by a booster dose on Day 29 of the same amount. The fourth test group was injected on Day 1 with 100 μL of reconstituted lyophilized vaccine Formulation C, which had a total mRNA content of 10 μg and was followed by a booster dose on Day 29 of the same amount. Immunogenicity was analyzed at three time points on Day 14, Day 28 and Day 43. Immunogenicity analysis was performed using standard indirect ELISA methods. The first test group injected with 0.5 μg of said vaccine does not show any significant increase in titre from Day 14 up to Day 43. A dose dependent exponential increase in titre was observed in test groups injected with 2 μg, 5 μg and 10 μg dose from Day 14 up to Day 43 [see FIG. 5A].

Example 7: Lyophilized mRNA Vaccine Neutralizing Antibody Responses

The SARS-COV-2 surrogate virus neutralization test [sVNT] was performed using the cPass SARS-COV-2 Neutralization Antibody Detection Kit [Genscript]. The assays were performed as per the manufacturer's protocol. Briefly, samples were diluted 10 times in dilution buffer. The diluted samples along with the positive and negative controls provided in the kit were incubated with equal volumes of 1000 fold HRP conjugated RBD supplied in the kit. Then the incubation was done at 37 °C for about 30 min. Then about 100 μL of all samples and controls are taken in the ACE-2 protein-coated wells provided with the kit. The reactions were allowed in dark for about 15 min at 37 °C. After 15 minutes the wells were washed 4 times before adding 100 μL of TMB substrate provided with the kit. The colours were allowed to develop for 15 min in the dark before the reactions were stopped with 50 μL HCl solution provided with the kit. The plate was read at 450 nm in a plate reader. Percent inhibition is calculated as (1−(OD of sample/OD of negative control))×100%.

Neutralizing antibody response of said lyophilized mRNA vaccine was tested in C57BL/6 mouse model. The study conducted in C57BL/6 mouse was done on a group of 24 animals, each group consisting of 6 animals. The first test group was injected on Day 1 with 100 μL of liquid vaccine which had a total mRNA content of 5 μg followed by a booster dose on Day 29 of the same amount. The second group was injected on Day 1 with 100 μL of reconstituted lyophilized vaccine Formulation A (with 10% sucrose) which had a total mRNA content of 5 μg and was followed by a booster dose on Day 29 of the same amount. The third test group was injected on Day 1 with 100 μL of reconstituted lyophilized vaccine Formulation B (with 20% sucrose) which had a total mRNA content of 5 μg and was followed by a booster dose on Day 29 of the same amount. The fourth test group was injected on Day 1 with 100 μL of reconstituted lyophilized vaccine Formulation (with 40% sucrose) which had a total mRNA content of 5 μg and was followed by a booster dose on Day 29 of the same amount. Neutralizing antibody responses were analyzed at four time points namely pre-bleed (2 days prior to priming injection), Day 14, Day 28 and Day 43. An increase in neutralizing antibody responses was observed in all test groups on Day 14 and Day 28 in comparison to the pre-bleed response. On day 43 a marked increase in neutralizing antibody responses was observed in the test group injected with frozen mRNA vaccine as well as three test groups injected with lyophilized mRNA vaccine formulations having 10%, 20% and 40% sucrose, respectively [see FIG. 5B].

We claim:

1. A method for the preparation of a freeze-dried formulation of mRNA, the method comprising:

(a) providing a liquid mixture having an mRNA adsorbed onto lipid nano-emulsion particles and a lyoprotectant in a glass vial, the lipid nano-emulsion particles comprising at least one cationic lipid compound;

(b) subjecting said liquid mixture to pre-cooling in a freeze drying chamber at a temperature between 5 and 25 °C;

(c) freezing said liquid mixture to a freezing temperature between −70 and −45 °C in said freeze drying chamber under a cooling rate between 0.07 and 1.2 °C/min and holding it for a time between 200 and 500 minutes forming a frozen mixture;

(d) reducing the pressure in said freeze drying chamber to a pressure below atmospheric pressure in two pressure reducing steps from 760 mTorr to about 100 mTorr and from 100 mTorr to about 35 mTorr and increasing temperature under three heating steps from about −60 °C to about −40 °C to about −20 °C and from about −20 °C to about 5 °C, at a heating rate between 0.05 and 0.9 °C/min and maintaining for a time between 1000 and 1600 minutes, thereby primary drying said frozen mixture;

(e) further heating said frozen mixture in said freeze drying chamber to a pressure further below atmospheric pressure from about 75 mTorr to about 35 mTorr and increasing temperature from about 5 °C to about 25 °C, thereby secondary drying said frozen mixture forming a lyophilized formulation; and (f) stoppering said glass vial and then equilibrating said freeze drying chamber to atmospheric pressure and temperature under nitrogen gas and removing said glass vial containing said lyophilized formulation for a pharmaceutical application wherein the lyophilized formulation exhibits stability at a temperature of about 2-8 °C for a period of 30 to 300 days while maintaining mRNA integrity and biological activity.

2. The method as claimed in claim 1, wherein said mRNA is an mRNA capable of expressing a protein molecule.

3. The method as claimed in claim 1, wherein said liquid mixture comprises an amount of said mRNA between 5 and 300 μg/mL.

4. The method as claimed in claim 1, wherein said lipid nano-emulsion particles further comprise squalene, polysorbate-80 and sorbitan monostearate.

5. The method as claimed in claim 1, wherein said lyoprotectant is selected from the group of carbohydrates consisting of mannitol, sucrose, glucose, mannose and trehalose.

6. The method as claimed in claim 1, wherein said liquid mixture comprises an amount of said lyoprotectant between 10 and 40 percent.

7. The method as claimed in claim 1, wherein said liquid mixture comprises an amount of said lyoprotectant between 20 and 40 percent.

8. The method as claimed in claim 1, wherein said pre-cooling is done at a cooling rate between 0.07 and 1.2 °C/min.

9. The method as claimed in claim 1, wherein under step (e) of secondary drying, a holding step at about 25 °C is maintained for a time between 400 and 700 minutes.

10. The method as claimed in claim 1, wherein under step (e) of secondary drying said temperature increase is done at a heating rate between 0.05 and 0.9 °C/min.

11. The method as claimed in claim 1, wherein said lyophilized formulation is stable at a temperature of about 5 °C for a time between 30 and 300 days.

12. The method as claimed in claim 1, wherein said lyophilized formulation shows immunogenicity in various animal models of mouse, rat and hamster.

13. The method as claimed in claim 1, wherein said lyophilized formulation maintains mRNA integrity in presence of RNase treatment.

14. A freeze-dried formulation obtained according to the method of claim 1 so as to form:

a stable mRNA complex in which said mRNA maintains its integrity upon storage at a temperature of about 5 °C for up to 300 days.

15. The freeze-dried formulation as claimed in claim 14, wherein said mRNA is capable of expressing a variant of the SARS-CoV-2 spike protein.

16. The freeze-dried formulation as claimed in claim 14, wherein said mRNA is a self-replicating or a non-replicating replicon mRNA transcript.

* * * * *